United States Patent [19]

Beineke

[11] Plant 4,964

[45] Dec. 14, 1982

[54] BLACK WALNUT TREE

[75] Inventor: Walter F. Beineke, West Lafayette, Ind.

[73] Assignee: Purdue Research Foundation, West Lafayette, Ind.

[21] Appl. No.: 254,905

[22] Filed: Apr. 16, 1981

[51] Int. Cl.[3] ..... A01H 5/03

[52] U.S. Cl. ..... Plt./32

[58] Field of Search ..... Plt./32

*Primary Examiner*—Robert E. Bagwill

*Attorney, Agent, or Firm*—John R. Nesbitt

[57] ABSTRACT

A new and distinct cultivar of black walnut tree (*Juglans nigra* L.) which is distinctly characterized by rapid growth rate, fairly strong central stem tendency, slightly earlier than average in time of leafing, and fair straightness thereby producing fair to good timber qualities. The new variety has fair nut bearing qualities. Nut crops are biennial and heavy in some years. Nut-bearing begins early in life of tree, average 2 nuts per cluster, and produces kernels which exceed about fifteen (15) percent of nut weight. The nuts are small and ripen late. The pistillate flowers mature mid-season while pollen maturity is very early to mid-season. In most years there is some overlap in female and male flowering. Flowering begins early in the life of the tree. This new variety of black walnut tree was discovered by the applicant near Bentonville in Fayette County, Ind., in a cultivated area. It occurred as a wild tree growing on land managed for timber-growing purposes and was discovered in the course of a search for unique and high quality black walnut trees to be utilized in breeding for outstanding timber producing potential. This selection has been designated as BW109 in records maintained on the performance of grafts made from the original selection and will be known henceforth as Fayette-1.

3 Drawing Figures

BACKGROUND OF THE INVENTION

After the original clone was selected, and assigned an identity number of BW109, the aforesaid tree was reproduced by collecting scions from it and grafting these onto common black walnut rootstocks at Martell Forest, Purdue University. These asexual reproductions ran true to the parent tree and to each other in all respects.

Figure 1:
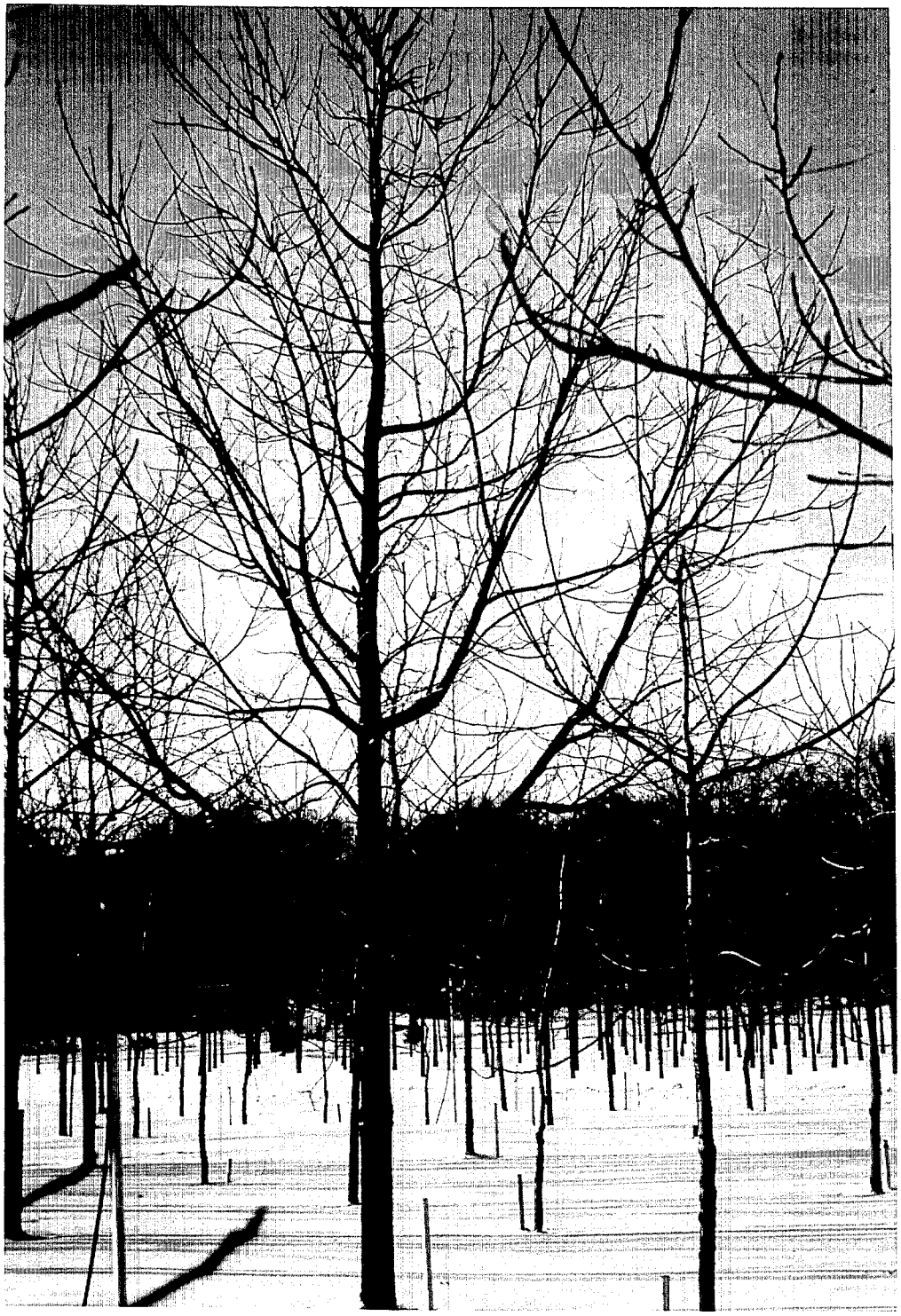
FIG. 1 is a photograph showing the timber form of Fayette-1.
Figure 2:
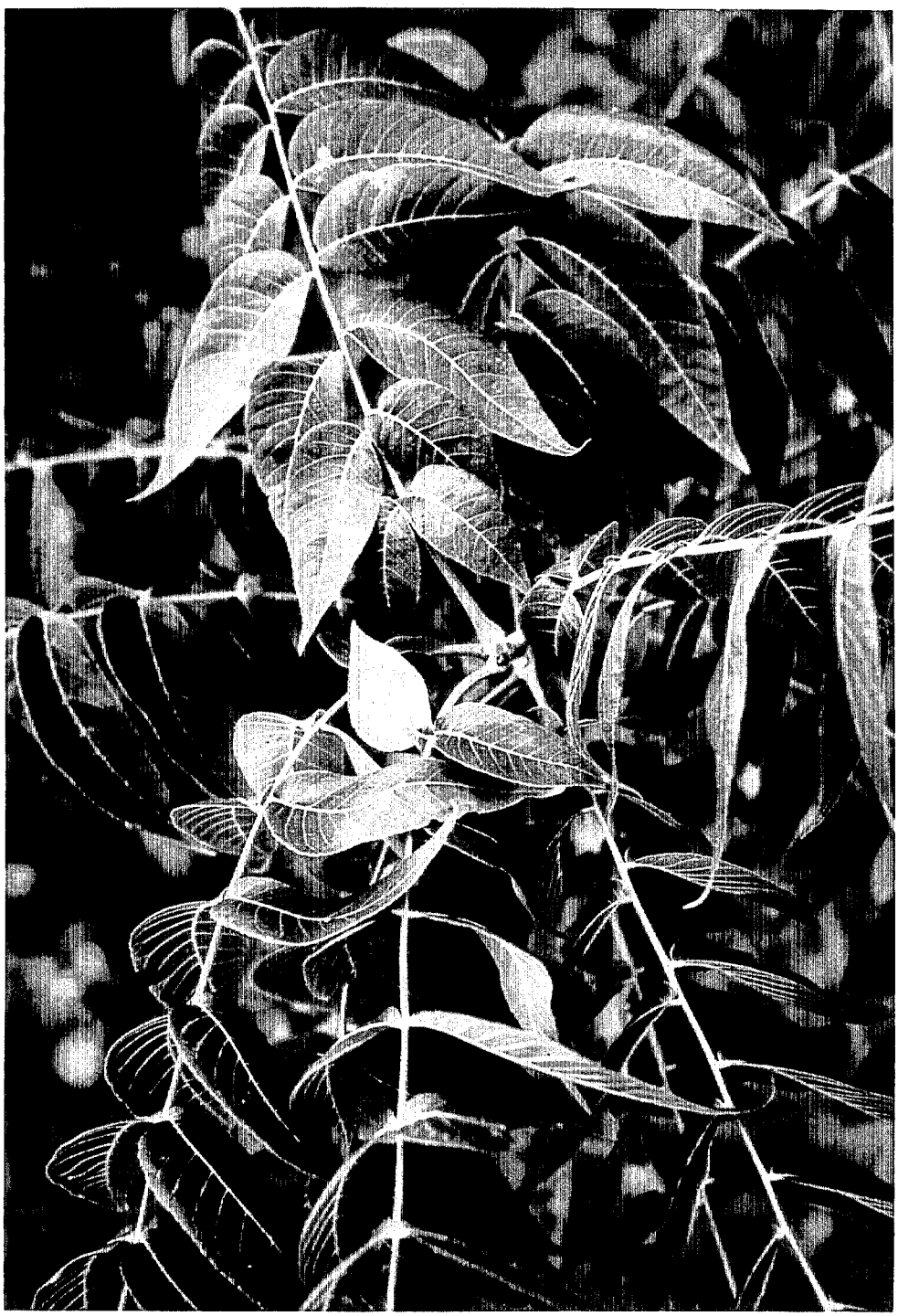
FIG. 2 is a photograph showing the leaves of Fayette-1.

The botanical details of this new and distinct variety of walnut tree are as follows:

Tree:

*Size.*—Large.

*Vigor.*—Vigorous.

*Growth rate.*—Rapid growth, nearly as fast as Purdue 1 and 2 — 12% larger in diameter than the average of selected clones planted the same year. 14% taller than the average, and 31% more cubic foot volume than the average.

*Form.*—Fair timber form, better than Purdue 2 but not as good as Purdue 1 and 3 — 17% straighter than average on a rating scale of 1 to 5. Average number of crooks. Fairly strong central stem tendency.

Trunk:

*Bark.*—Dark brown to gray.

*Texture.*—Interlacing ridges.

Branches:

*Diameter.*—Average.

*Length.*—Shorter than average.

*Branch angle.*—Lower branches — steep — 67 deg.

*Foliage.*—Quantity — abundant. Density — heavy.

Leaves:

*Compound leaves.*—Size — shorter than average; average length — 13¼".

*Leaflets.*—Size — smaller than average; average length — 3¼"; average width — 1¼"; average number of leaflets — 18; shape — lanceolate; acutely pointed. Thickness — thin; Texture — smooth; Margin — serrated; Petiole — short; Color — Topside — dark green; Underside — light green.

*Anthracnose resistance.*—Excellent — much better than average on a rating scale of 1 to 5.

*Time of leafing.*—Early — average 1 to 2 days earlier or 12% earlier than average.

Flowering habit:

*Age at which tree starts producing catkins.*—Early.

*Number of catkins produced.*—Abundant.

*Size of catkins.*—Very long.

*Time of pollen shed.*—Begins very early but over long period.

*Age at which time tree starts producing pistillate flowers.*—Early.

*Number of pistillate flowers produced by young trees.*—Abundant.

*Number of pistillate flowers produced by mature trees.*—Abundant.

*Lateral shoots producing pistillate flowers.*—Seldom.

*Number of pistillate flowers per inflorescence.*—2 and 3.

*Timing of pistillate flower receptivity.*—Mid-season.

*Coincidence of staminate and pistillate bloom.*—Overlaps.

Nut crop:

*Bearing.*—Biennial.

*Productivity.*—Heavy.

*Ripening period.*—Late.

*Evenness of maturity (period between first and last nuts are ready for harvest).*—Even.

*Quality.*—Fair.
*Distribution of nuts on tree.*—Throughout.

Hull:
*Outer surface.*—Warty.
*Form.*—Pointed blossom end.
*Thickness.*—Thin.
*Size.*—Small; average length — 2-3/32"; average diameter in suture plane — 1¾"; average diameter cheek to cheek — 1-15/16".

Nut:
*Size.*—Small; average length — 1⅜"; average diameter in suture plane — 1-3/32"; average diameter cheek to cheek — 1⅜".
*Uniformity of size.*—Some variation.
*Form.*—Oblong.
*Blossom end.*—Rounded.
*Basal end.*—Slightly pointed.
*Weight.*—Dry weight of ten nuts — 120.3 gm; dry weight of ten kernels — 17.6 gm; average percentage kernel to nut — 14.6%.
*Thickness of shell.*—Thick.
*Fill.*—Poor.

Kernel:
*Size.*—Large.
*Plumpness.*—Plump.
*Shrivel.*—None.
*Flavor.*—Good.
*Color.*—Light.

The walnut tree and its nuts herein described may vary in slight detail due to climatic and soil conditions under which the variety may be grown; the present description being of the variety as grown near West Lafayette, Ind.

I claim:

1. A new and distinct variety of black walnut tree substantially as illustrated and described, which has fair to good timber quality, is fast growing, has fairly strong central stem tendency; earlier than average in time of leafing, pistillate flowers mid-season, pollen sheds early to mid-season, produces biennial crops of small nuts; averages 2 per cluster, the percentage of weight of kernel to nut averages approximately 15 percent; nut bearing begins early in life of tree.

* * * * *